United States Patent [19]
Islava

[11] Patent Number: 6,067,985
[45] Date of Patent: May 30, 2000

[54] ADJUSTABLE ENDOTRACHEAL TUBE HOLDER

[76] Inventor: Steven T. Islava, 315 Marigold, Corona del Mar, Calif. 92625

[21] Appl. No.: 08/805,634

[22] Filed: Feb. 26, 1997

Related U.S. Application Data

[63] Continuation-in-part of application No. 08/608,130, Feb. 28, 1996, abandoned.

[51] Int. Cl.[7] .............................. A61M 16/00; A62B 9/06
[52] U.S. Cl. ............................... 128/207.17; 128/207.14; 128/DIG. 26; 128/200.26
[58] Field of Search ................. 128/207.14, 207.17, 128/912, DIG. 26, 200.26

[56] References Cited

U.S. PATENT DOCUMENTS

| | | | |
|---|---|---|---|
| 3,568,679 | 3/1971 | Reif | 128/DIG. 26 |
| 4,683,882 | 8/1987 | Laird | 128/207.17 |
| 4,742,824 | 5/1988 | Payton et al. | 128/DIG. 26 |
| 4,832,019 | 5/1989 | Weinstein et al. | 128/207.17 |
| 4,906,234 | 3/1990 | Voychehovski | 128/207.17 |
| 5,105,807 | 4/1992 | Kahn et al. | 128/DIG. 26 |
| 5,345,931 | 9/1994 | Battaglia, Jr. | 128/207.17 |
| 5,419,319 | 5/1995 | Werner | 128/207.17 |
| 5,437,273 | 8/1995 | Bates et al. | 128/207.17 |

*Primary Examiner*—Kimberly L. Asher
*Attorney, Agent, or Firm*—Harold L. Jackson

[57] ABSTRACT

An endotracheal tube-holder assembly that includes an arcuate track member and a pair of face plates mounted at the free ends thereof for engaging the opposite sides or cheeks of a patient's face, and wherein an adjustable holding block assembly is slidably mounted on the track member which defines a support housing that includes a tube holding block and a bite block support in which a removable bite block is mounted.

33 Claims, 3 Drawing Sheets

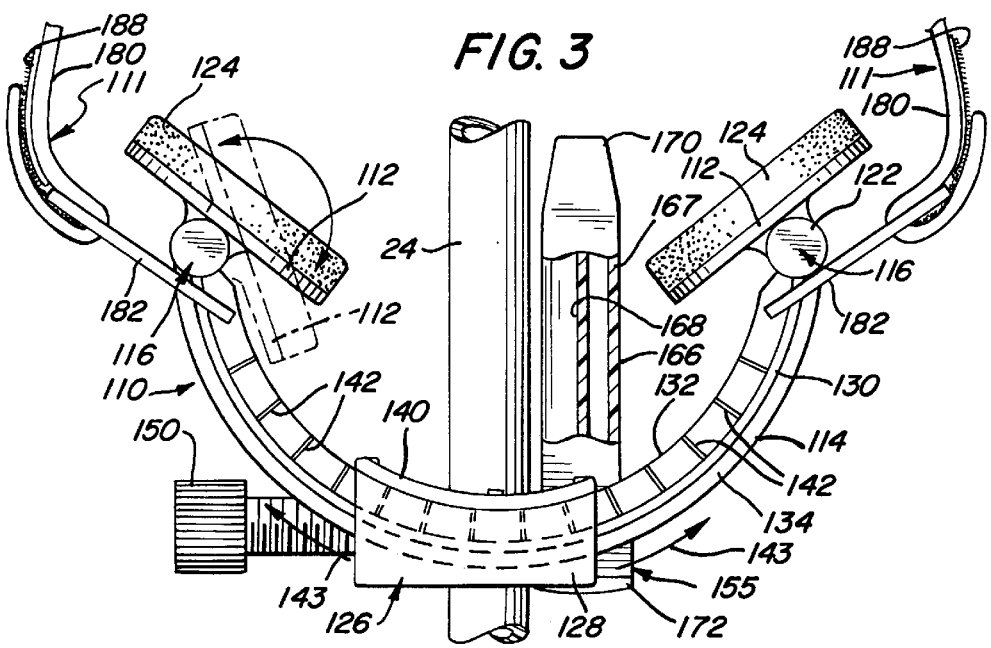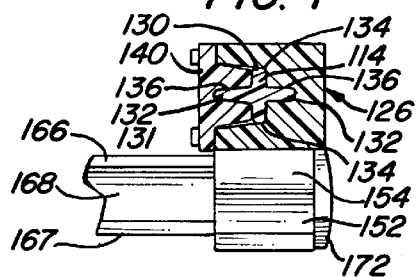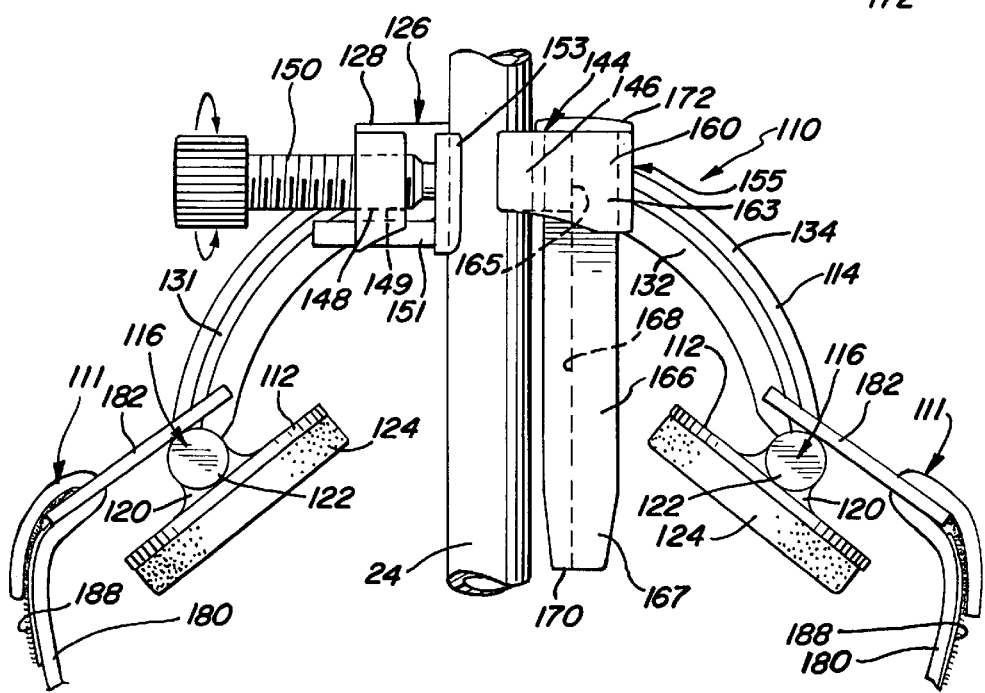

ADJUSTABLE ENDOTRACHEAL TUBE HOLDER

RELATED APPLICATION

This is a continuation-in-part of application Ser. No. 08/608,130, filed Feb. 28, 1996, now abandoned, for ADJUSTABLE ENDOTRACHEAL TUBE HOLDER.

BACKGROUND OF THE INVENTION

1. Field of the Invention

The present invention relates generally to an endotracheal tube holder assembly and more particularly to a holding block assembly that permits the tube to be adjustably positioned with respect to a patient's mouth.

2. Description of the Prior Art

It should be noted that the present application is an improved embodiment over the tube holder disclosed in my pending application Ser. No. 08/323,159 filed Oct. 14, 1994 for an ENDOTRACHEAL TUBE HOLDER, which in turn is a continuation-in-part of Ser. No. 234,540 filed Apr. 28, 1994, now U.S. Pat. 5,402,776 issued to the present applicant.

Endotracheal tube devices are used under several conditions such as in the ventilation of a patient during anesthesia, resuscitation as well as during critical care that commonly arise not only in the hospital but also during the time when a patient is being transported.

As is well known in the art, various problems and difficulties are encountered in providing suitable means for securing an endotracheal tube in a simple and positive manner to a tube holding device that is generally a part of a mouth piece of the face plate assembly.

Many types of securing arrangements have been tried in the prior art which very often included simply mounting the tube in place with adhesive tape that was applied to the tube and several areas of the patient's face. Some endotracheal tubes were mounted in a face plate that included a bite block whereby the patient was required to grip the bite block with his or her teeth. However, other prior art tube holders have included locking means for securing the endotracheal tube to the face plate of the tube holder.

For typical examples of prior art endotracheal tube holders one may refer to those disclosed in the following U.S. patents:

U.S. Pat. No. 4,867,154 issued to A. B. Potter, et al;
U.S. Pat. No. 4,832,019 issued to B. Weinstein;
U.S. Pat. No. 4,744,358 issued to G. E. McGinnis;
U.S. Pat. No. 4,537,192 issued to B. R. Foster;
U.S. Pat. No. 4,449,527 issued to D. L. Hinton;
U.S. Pat. No. 4,249,529 issued to J. Nestor, et al.
U.S. Pat. No. 5,402,776 issued to Steve Islava In addition to the above patents see U.S. Pat. No. 5,490,504 ("'504 patent") which issued to D. W. Vrona et al. The '504 patent teaches an endotracheal tube attachment device in which a flexible track strip is secured across the upper lip and adjacent cheek area of a patient by means of an adhesive. Such an adhesive, in intimate contact with a patient's skin for a prolonged period, irritates the skin and often results in a breakdown of the skin tissue. To properly provide long term care of patients, depending upon an endotracheal tube, it is necessary to clean the oral cavity frequently, e.g., every 2–4 hours, to prevent or inhibit the development of oral pneumonia. The '504 track strip would not appear to be conducive to such cleaning practices because the adhesive would be wetted by such secretions, thereby providing a further irritant to the skin underlaying the track and adhesive. Furthermore, the tube attachment device disclosed in the '504 patent is not useable, as a practical matter, with patients that normally wear dentures since, in the absence of such dentures, there is inadequate support for the track strip.

There is a need for an adjustable endotracheal tube holder suitable for long term use which overcomes the disadvantages of the prior art.

BRIEF SUMMARY AND OBJECTS OF THE INVENTION

An endotracheal tube-holder assembly in accordance with the present invention comprises a pair of oppositely disposed face plates that can either be fixedly or hingedly attached to the opposite ends of a rigid curved track. A holding block assembly comprising a housing is slidably mounted on the track so as to be adjustably positioned over the patient's mouth once the face plates and track are mounted on the patient's head by means of a suitable headband.

Thus, the present invention has for an important object to provide a unique endotracheal tube-holder assembly that includes an arcuate track member which is held in a spaced relationship with the area surrounding the patient's mouth by a pair of face plates mounted at each end of the track. The spacing between the track member and the patient's mouth accommodates the circulation of air between the track and the area surrounding the mouth thereby minimizing the accumulation of secretions in such area. The arcuate track is arranged to slidably support a holding block assembly that includes a means for attaching an endotracheal tube and a means for removably supporting a bite block.

Another object of the invention is to provide a pair of face plates that are respectively mounted to the opposite ends of the track so to be positioned on a patient's face to engage the respective cheeks thereof. Still another object of the present invention is to provide a holding block and rail assembly which allows the endotracheal tube to be adjustably moved along the rail assembly in a longitudinal direction, (across the patient's mouth) whereby the tube can be located at a desired position with respect to a patient's mouth. Yet another object of the present invention is to provide an endotracheal tube holder that will accommodate a number of different sizes of tubes, whereby a selected tube can be firmly placed within the housing of the block assembly.

Still another object of the invention is to provide an endotracheal tube holder that includes a bite-block mounting unit formed with a V-shaped projection adapted to receive a corresponding V-shaped channel formed longitudinally in a removable bite block, and wherein the bite block further aids in the alignment of the tube within the mouth of the patient.

A further object of the present invention is to provide an endotracheal tube holder assembly, wherein the face plates can be either fixedly mounted to the track or hingedly attached to fit a specific contour of the individual's face without interfering with the positioning of the endotracheal tube, and wherein each face plate is provided with a foam pad to protect the patient from inadvertent injury of discomfort.

Still another object of the present invention is to provide a tube holder of this character that includes an adjustable headband that is arranged to be connected at the opposite ends of the track member by means of buckle members or to the face plates, wherein the headband is adjustably attached to the respective buckles or face plates by means of VELCRO® or other suitable like securing material.

A still further object of the invention is to provide a tube holder of this character that is simple in construction and relatively inexpensive to manufacture.

The characteristics and advantages of the invention are further sufficiently referred to in connection with the accompanying drawings, which represent one or more embodiments. After considering these examples, skilled persons will understand that variations may be made without departing from the principles disclosed; and I contemplate the employment of any structures, arrangements or modes of operation that are properly within the scope of the appended claims.

BRIEF DESCRIPTION OF THE DRAWINGS

With the above and related objects in view, the invention consists in the details of construction and combination of parts, as will be more fully understood from the following description, when read in conjunction with the accompanying drawings and numbered parts.

FIG. 3 is a top plan view of the endotracheal tube holder assembly;

FIG. 4 is a bottom plan view thereof;

FIG. 5 is a cross-sectional view taken substantially along line 5—5 of FIG. 2.

DETAILED DESCRIPTION OF THE INVENTION

Figure 1:
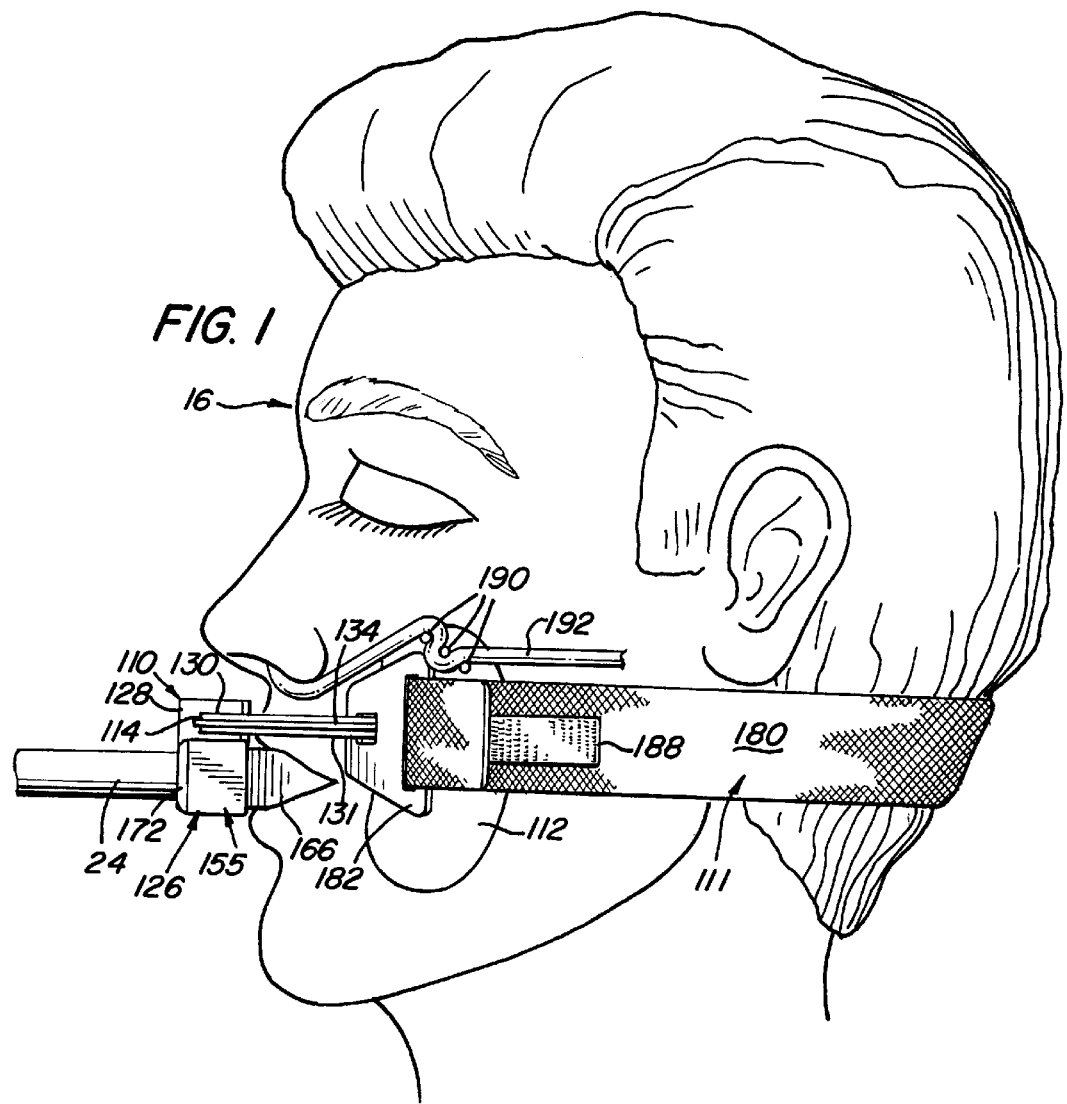
FIG. 1 is a pictorial view of an endotracheal tube holder assembly that illustrates the present invention mounted in an operative position as worn by a patient.

Referring more particularly to FIG. 1, there is shown the preferred embodiment of the present invention defined as an endotracheal tube holder assembly, generally indicated at 110, which is securely mounted to the patient's head 16 by means of an adjustable attaching means defined by a headband 111.

The endotracheal tube-holder assembly 110 comprises a pair of oppositely disposed face plate members 112, a foam pad 124 being mounted to the face engaging side of each face plate. The face plates are shown as being attached to a substantially rigid curved (e.g., semicircular) bridge or track 114 by hinge means, designated generally at 116, comprising a pair of hinge members 118, each hinge member being formed at each respective end of track 114. Accordingly, each face plate member 112 is provided with a pair of hinge members 120 that are arranged to receive corresponding hinge members 118 by means of a hinge pin 122. Each face plate is provided with a suitable configuration and is covered with the soft foam pad 124. The face pads (i.e., the plate members 112 and the pads 124) engage the respective cheeks of the face, while holding the track 114 in spaced relationship with the patient's face thereby accommodating the circulation of air between the track and the area surrounding the patient's mouth, as is illustrated in FIGS. 1 and 3. The area surrounding the patient's mouth is thus unencumbered. Maintaining the track 114 out of contact with the patient's mouth and lip area eliminates skin irritation of that area and enables the oral cavity to be cleaned while minimizing the deposit of secretions on any part of the holder which is in intimate contact with the patient's face.

It should be noted that it is contemplated that the face plates can be fixedly attached to track 114 at a suitable angle, thereby eliminating the hinge means if desired as will be explained in connection with FIG. 6. This would allow for a simpler construction of the assembly and result in some savings in manufacturing costs.

An adjustable holding block assembly, designated generally at 126, comprises a housing 128 which is adapted to be slidably mounted on track 114 by means of a longitudinal passageway. Track 114 is formed with vertically disposed rails 130 and 131, and horizontally disposed rails 132 and 133, (FIG. 4), whereby the position of the rails define a substantially cross-like configuration. The passageway is provided with grooves 134 and 136 that correspond to the respective rails 132 and 133, as illustrated in FIG. 4, the grooves being formed in the housing 128 and cover member 140. The upper surface of rail 132 is provided with markings or notches 142 so as to allow accurate positioning of the adjustable holding block assembly 126 with respect to the notches and to the patient's mouth. This arrangement allows one to adjust holding block assembly 126 laterally along the arcuate track 114 in either direction, as indicated in FIG. 3 by arrows 143, whereby tube 24 can be positioned in the center or to either side of the patient's mouth.

Figure 2:
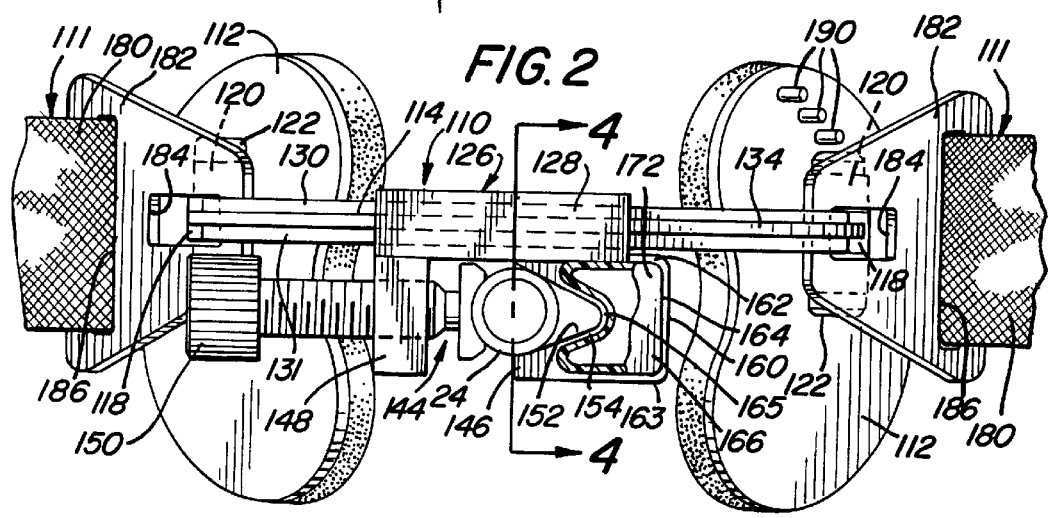
FIG. 2 is a front-elevational view of the endotracheal tube holder assembly.

Housing 128 is further formed with a tube-holding means or fixture 144 which comprises a bracket 146, an internally threaded depending member 148 (FIG. 2) and thumb screw 150 threadably received in the member 148. Both the bracket 146 and depending member 148 are integrally formed as part of housing 128. The depending member 148 is provided with a slot 149 to receive a pin 151 extending from the thumbscrew engagement head 153 of the thumbscrew 150 to prevent the head 153 from rotating. The tube holding bracket is provided with a substantially V-shaped securing notch 152 defined by a pair of converging wall members 154 in which endotracheal tube 24 is removably secured, as illustrated in FIGS. 2 and 4.

A bite-block support, generally designated at 155, is also formed as an integral part of adjustable housing 126 and is defined by a tubular frame member 160 that comprises the inner sides of converging wall members 154, a top wall 162, a bottom wall 163, and an outer side wall 164. The converging walls 154 extend inwardly of the tubular frame member 160, whereby the converging wall members 154 and the apex thereof define a guide member 165 for a bite block 166.

Accordingly, it is important to note that bite block 166 is removably mounted to adjustable housing 126 and is not fixedly secured or formed as an integral part of the endotracheal tube-holder assembly 110. Bite block 166 is formed having a matching configuration to that of the tubular frame member. That is, bite member 160 is formed as an elongated body 167 having a channel 168 adapted to receive guide member 165. Bite block 166 includes a tapered inserting end 170 and a cap end 172 which allow the bite block to be easily inserted or removed as needed.

Figure 6:
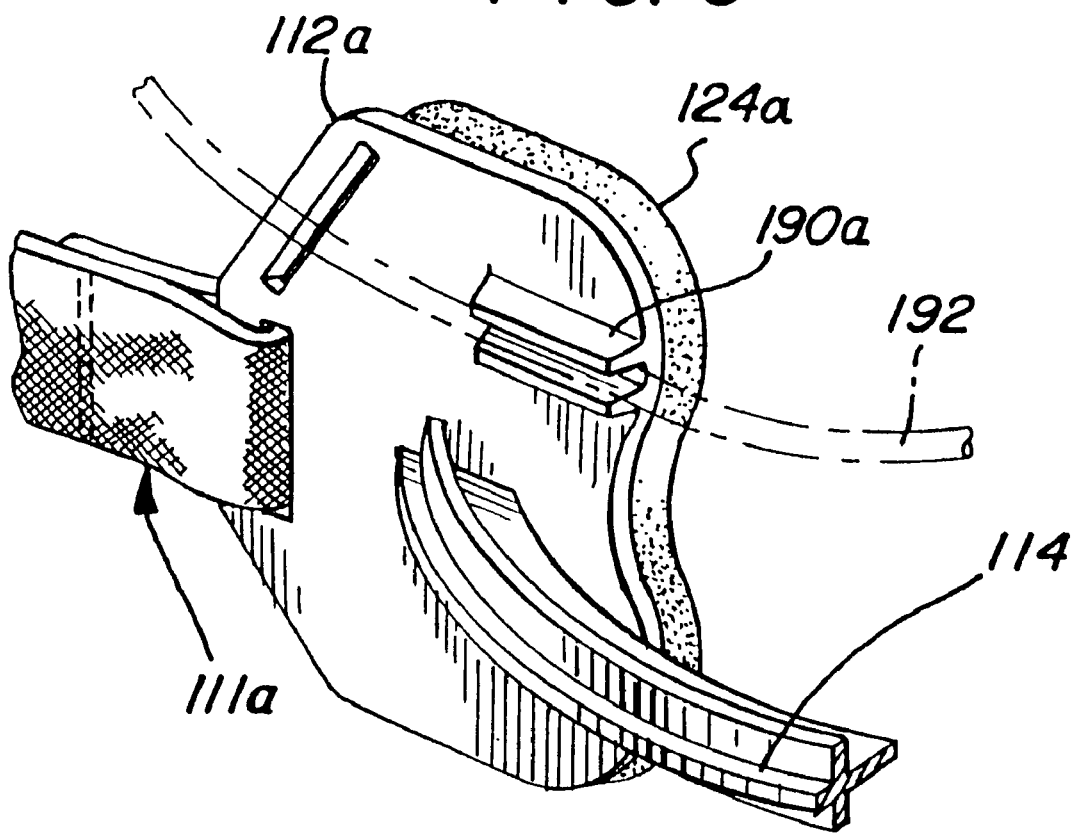
FIG. 6 is a perspective view showing an alternative face pad arrangement in which the face pads are mounted directly on the ends of the tube holder track, thereby eliminating the need for a hinged connection.

Referring now to FIG. 6, a face plate member 112a (carrying pad 124a) is shown as being mounted directly to one end of the track 114 thereby eliminating the need for hinges. It is to be understood that while only one face plate member is shown a corresponding face plate member is to be mounted on the other end of the track 114. Preferably the face plate members 112a and the track 114 are molded as an integral unit.

Referring again to FIGS. 1–5, headband 111 (or 111a in FIG. 6) is defined by at least one or more elongated straps 180, made from a soft material which is adjustably attached to the adjacent the ends of curved track 114 by means of buckles or clasp members 182 formed with slotted openings 184. These buckles are hooked around the rails of the track, as illustrated in FIGS. 1, 2, 3 and 5. Each buckle is further provided with a slot 186 in which each respective end of strap 180 is received. A securing means defined by a strip 188 formed from a hook-type fastening material is fixedly attached to each respective end of strap 180 so that the strip can be secured to the strap, whereby headband 111 can be readily adjusted to the patient's head.

At least one of the face plates 112 or 112a is provided with a tube support means that can be defined by plurality of support pins 190 or channel member 190a positioned and arranged on the outer surface thereof to receive and support a nasogastric tube 192, as illustrated in FIGS. 1 and 6.

An important advantage of the present invention is the positioning of the track 114 and the housing 128 at a suitable distance (e.g., about ½" to 1½") from the patients face. The adjustability of the housing 128 on the track 114 is also important in that it allows a nurse, doctor, or other health care provider to move the housing and tube relative to the patient's mouth to view different portions of the lips, tongue and/or interior of the mouth and to clean the oral cavity without removing the tube from the patient's trachea. The track 114 and housing 122 are preferably made of a rigid plastic material, e.g., polyethylene, such as "DELRIN"™.

The foregoing should only be considered as illustrative of the principles of the invention. Further, since numerous modifications and changes may readily occur to those skilled in the art, it is not desired to limit the invention to the preferred embodiment as shown and described, and accordingly, all suitable modifications and equivalents may be resorted to, falling within the scope of the claimed invention.

What is claimed is:

1. An endotracheal tube-holder apparatus for positioning a tube within a patient's trachea, the tube holder apparatus comprising:
   a curved track adapted to be positioned adjacent the mouth of a patient;
   a pair of face pads, the pads being mounted at opposite ends of the track and arranged to support the track in spaced relationship to the patient's mouth whereby the area surrounding the patient's mouth is unencumbered for accommodating the circulation of air between the track and said area;
   a holding block assembly adjustably mounted on said track relative to the mouth of a patient;
   a tube holding fixture formed as part of said holding block assembly for releasably holding an endotracheal tube;
   a bite-block support formed as part of said holding block assembly for receiving a bite-block; and
   means for attaching said endotracheal tube-holder apparatus on a patient's head.

2. An endotracheal tube-holder apparatus as recited in claim 1, wherein each of said pads is carried by a face plate with each plate mounted to the track.

3. An endotracheal tube-holder apparatus as recited in claim 2, further including a bite block adapted to be removeably positioned in the bite block support.

4. An endotracheal tube-holder apparatus as recited in claim 3, wherein said face plates are fixedly attached to said track means and angularly disposed thereto.

5. An endotracheal tube-holder apparatus as recited in claim 2, wherein said track has a cross-sectional configuration and wherein said holding block assembly comprises a housing having a longitudinal passageway with a cross-sectional configuration to match the cross-sectional configuration of said track.

6. An endotracheal tube-holder apparatus as recited in claim 5, wherein said tube holder fixture includes a tube holding bracket and a depending member integrally formed with said housing.

7. An endotracheal tube-holder apparatus as recited in claim 6, wherein said tube holding fixture further includes a thumb screw.

8. An endotracheal tube-holder apparatus as recited in claim 7, wherein said tube holding bracket includes a depending member having a slot formed therein, and wherein said thumb screw includes a rotatable movable head formed with a slide pin, the slide pin being adapted to be positioned in said slot of said depending member, whereby said head is prevented from rotating as said thumb screw is rotated to engage said head with said endotracheal tube.

9. An endotracheal tube-holder apparatus as recited in claim 8, wherein said tube holding bracket is formed having a V-shaped notch aligned with said head of said thumb screw, whereby said endotracheal tube is secured in said V-shaped notch.

10. An endotracheal tube-holder apparatus as recited in claim 9, wherein said V-shaped notch is defined by a pair of converging wall members that are joined together to define an extended apex member that further defines said guide member in said tubular frame member.

11. An endotracheal tube-holder apparatus as recited in claim 10, wherein at least one of said face plates is provided with a tube mounting means which is positioned thereon to receive and support an elongated tube.

12. An endotracheal tube-holder apparatus as recited in claim 11, wherein said tube mounting means comprises a plurality of pins.

13. An endotracheal tube-holder apparatus as recited in claim 11, wherein said tube mounting means comprises a channel member.

14. An endotracheal tube-holder apparatus as recited in claim 11, wherein said means for attaching said endotracheal tube-holder apparatus on the patient's head comprises at least one elongated headband.

15. An endotracheal tube-holder apparatus as recited in claim 14, wherein said headband is attached to said track means by at least one buckle mounted to said track means.

16. An endotracheal tube-holder apparatus as recited in claim 14, wherein said headband is attached to said face plates.

17. An endotracheal tube-holder apparatus as recited in claim 5, wherein said bite-block support comprises a tubular frame member having a guide member extending inward of said tubular frame member, whereby said bite block is formed with a channel to receive said guide member, and wherein said bite block is removably inserted and supported within said frame member.

18. An endotracheal tube-holder apparatus as recited in claim 17, wherein said cross-sectional configuration of said track is defined by a pair of vertically disposed rail members and a pair of horizontally disposed rail members, and wherein said passageway of said housing is formed having corresponding vertical grooves and horizontal grooves in which said corresponding rail members are respectively received, whereby said holding block assembly is slidably adjusted to a selective position along said track so as to position said endotracheal tube at the center or at either side of a patient's mouth.

19. An endotracheal tube-holder apparatus as recited in claim 18, wherein at least one of said horizontal rails is provided with surface markings, whereby said holding block assembly is accurately positioned.

20. An endotracheal tube-holder apparatus as recited in claim 2, wherein said track includes a hinge means hingedly connecting said face plates to said track means, whereby said face plates and pads carried thereby adjustably fit and engage a contour of the respective sides of the patient's face.

21. An endotracheal tube-holder apparatus as recited in claim 2 wherein the curved track is defined as being substantially semicircular.

22. An endotracheal tube-holder apparatus for securing an endotracheal tube relative to a patient's mouth, the tube holder comprising:

a track formed of a substantially rigid material and having a curved configuration;

a face plate formed on each end of the track a pad secured to each face plate:

the pads being arranged to engage the cheek areas of a patent on opposite sides of a patient's mouth to support the track so that the track is spaced from and not in contact with the patient's mouth to allow air to circulate between the track and the area surrounding a patient's mouth;

a holding block assembly adjustable mounted along said track relative to the mouth of a patient;

a tube holder fixture formed as part of said holding block assembly for securing a tube in said tube holder; and means for attaching said endotracheal tube-holder apparatus on a patient's head.

23. An endotracheal tube-holder apparatus as recited in claim 22, wherein said curved configuration of said track means is defined as being approximately semicircular.

24. An endotracheal tube-holder apparatus as recited in claim 22, wherein said track has a cross-sectional configuration and wherein said holding block assembly is defined as a housing having a longitudinal passageway with a cross-sectional configuration to match the cross-sectional configuration of said track.

25. An endotracheal tube-holder apparatus as recited in claim 24, wherein said tube holder fixture comprises a tube holding bracket and a member spaced therefrom, the bracket and member being integrally formed with said housing and a thumb screw threaded into the spaced member for pressing the tube against the bracket.

26. An endotracheal tube-holder apparatus as recited in claim 25, further including a bite-block support formed integrally with the holding block assembly.

27. The endotracheal tube-holder of claim 26 wherein the bite-block support comprises a tubular frame member having a guide member extending inward of said tubular frame member, and wherein said bite block is formed with a channel to receive said guide member, the bite-block being removably inserted and supported within said frame member.

28. An endotracheal tube-holder apparatus comprising:

a substantially rigid track having a generally semicircular configuration;

a face plate mounted at each end of said track so that the face plates are oppositely disposed to each other;

a face pad secured to each face plate:

the face pads being arranged to engage the cheeks of a patient and position the track in a spaced relationship with the patient's mouth so that air can circulate between the track and the area surrounding a patient's mouth, the face plates and pads providing the sole support for the track;

a holding block assembly adjustable mounted on said track means relative to the mouth of a patient;

a tube holding means formed as part of said holding block assembly;

means for securing a tube in said tube holding means;

a bite-block support means formed as part of said holding block assembly;

a bite block arranged to be removably mounted in said block-support means; and means for attaching said endotracheal tube-holder apparatus on the patient's head.

29. An endotracheal tube-holder apparatus as recited in claim 28, wherein said track is formed having an arcuate configuration.

30. An endotracheal tube-holder apparatus as recited in claim 29, wherein said track has a cross-sectional configuration and wherein said holding block assembly being defines as a housing having a longitudinal passageway with a cross-sectional configuration to match the cross-sectional configuration of said track.

31. An endotracheal tube-holder apparatus as recited in claim 30, wherein said tube holder fixture includes a tube holding bracket and a depending member integrally formed in said housing.

32. An endotracheal tube-holder apparatus as recited in claim 31, wherein said tube holding fixture further includes a thumb screw.

33. An endotracheal tube-holder apparatus as recited in claim 31, wherein said bite-block support means comprises a tubular frame member having a guide member extending inwardly of said tubular frame member, whereby said bite block is formed with a channel to receive said guide member, and wherein said bite block is removably inserted and supported within said frame member.

* * * * *